(12) United States Patent
Buc et al.

(10) Patent No.: US 12,403,040 B2
(45) Date of Patent: Sep. 2, 2025

(54) SYSTEM FOR PROJECTING A PATTERN OF INTEREST ONTO A RETINAL AREA OF A HUMAN EYE

(71) Applicant: La Science SAS, Paris (FR)

(72) Inventors: Guillaume Buc, Bures sur Yvette (FR); Xavier Beuque, Le Mans (FR); Vincent Bismuth, Paris (FR); Martin Deterre, Paris (FR)

(73) Assignee: La Science SAS, Paris (FR)

( * ) Notice: Subject to any disclaimer, the term of this patent is extended or adjusted under 35 U.S.C. 154(b) by 482 days.

(21) Appl. No.: 17/593,274

(22) PCT Filed: Mar. 27, 2020

(86) PCT No.: PCT/EP2020/058873
§ 371 (c)(1),
(2) Date: Sep. 14, 2021

(87) PCT Pub. No.: WO2020/193796
PCT Pub. Date: Oct. 1, 2020

(65) Prior Publication Data
US 2022/0192885 A1    Jun. 23, 2022

(30) Foreign Application Priority Data
Mar. 28, 2019   (WO) ................. PCT/EP2019/057965

(51) Int. Cl.
*A61F 9/08*      (2006.01)
*A61B 3/00*      (2006.01)
(Continued)

(52) U.S. Cl.
CPC .............. *A61F 9/08* (2013.01); *A61B 3/0008* (2013.01); *A61N 5/0622* (2013.01); *G02B 26/08* (2013.01);
(Continued)

(58) Field of Classification Search
None
See application file for complete search history.

(56) References Cited

U.S. PATENT DOCUMENTS 5,777,715 A    7/1998  Kruegle et al.
5,796,526 A *  8/1998  Anderson ............... B41J 2/465
                                                 359/671

(Continued)

FOREIGN PATENT DOCUMENTS

JP    09-122077 A     5/1997
JP    2018068867 A    5/2018
(Continued)

OTHER PUBLICATIONS

"Micron Image-Guided Laser", Phoenix-Micron, Inc., first downloaded Jan. 6, 2025.
(Continued)

*Primary Examiner* — Kennedy Schaetzle
(74) *Attorney, Agent, or Firm* — Jeffrey Schox; Annabel Imbrie-Moore (57) ABSTRACT

The present invention pertains to a system for projecting a pattern of interest onto a retinal area of a human eye, containing a carrying frame for being worn by a patient, a camera for capturing an image, a projector device for projecting a pulsed light beam reflecting a pattern of interest into a human eye, and a processor device being in communication with the camera and the projector device, wherein the processor device is adapted for converting the image captured by the camera into the pattern of interest being basis for the pulsed light beam, wherein the projector device and the camera are attached to the carrying frame.

15 Claims, 4 Drawing Sheets

(51) Int. Cl.
*A61N 5/06* (2006.01)
*G02B 26/08* (2006.01)
*G02B 27/00* (2006.01)
*G02B 27/01* (2006.01)

(52) U.S. Cl.
CPC ..... *G02B 26/0833* (2013.01); *G02B 27/0093* (2013.01); *G02B 27/0172* (2013.01); *A61N 2005/0648* (2013.01)

(56) References Cited

U.S. PATENT DOCUMENTS

| | | | |
|---|---|---|---|
| 6,030,376 A | 2/2000 | Arashima et al. | |
| 7,311,723 B2 | 12/2007 | Seibel et al. | |
| 8,956,396 B1* | 2/2015 | Friend | A61N 5/0622 607/88 |
| 12,061,332 B2 | 8/2024 | Durban et al. | |
| 2002/0087202 A1* | 7/2002 | Chow | A61F 9/08 607/53 |
| 2002/0101568 A1* | 8/2002 | Eberl | G02B 27/0172 351/211 |
| 2004/0116980 A1* | 6/2004 | Ohta | A61F 9/0017 607/54 |
| 2005/0015120 A1* | 1/2005 | Seibel | A61F 9/08 606/4 |
| 2006/0158639 A1 | 7/2006 | Campin et al. | |
| 2006/0168859 A1* | 8/2006 | Pombo | G02B 7/023 40/611.07 |
| 2007/0159599 A1 | 7/2007 | Yamada | |
| 2008/0002262 A1 | 1/2008 | Chirieleison | |
| 2009/0005691 A1 | 1/2009 | Huang et al. | |
| 2009/0210039 A1 | 8/2009 | Boyden et al. | |
| 2011/0004272 A1 | 1/2011 | Seibel et al. | |
| 2011/0127405 A1 | 6/2011 | Grossman et al. | |
| 2012/0098972 A1* | 4/2012 | Hansen | H04N 23/45 348/E5.09 |
| 2013/0278497 A1 | 10/2013 | Takagi et al. | |
| 2013/0289668 A1 | 10/2013 | Nirenberg et al. | |
| 2014/0050386 A1 | 2/2014 | Humayun et al. | |
| 2015/0238362 A1* | 8/2015 | Chayet | A61F 9/08 348/63 |
| 2015/0289762 A1 | 10/2015 | Popovich et al. | |
| 2018/0160048 A1* | 6/2018 | Rainisto | G06F 3/013 |
| 2018/0304095 A1 | 10/2018 | Register et al. | |
| 2019/0384063 A1* | 12/2019 | Oliver | G02B 27/0172 |
| 2021/0031051 A1 | 2/2021 | Kubota et al. | |
| 2021/0059520 A1 | 3/2021 | Nankivil | |
| 2022/0197022 A1 | 6/2022 | Deterre et al. | |
| 2023/0110912 A1 | 4/2023 | Oggenfuss et al. | |

FOREIGN PATENT DOCUMENTS

| | | |
|---|---|---|
| WO | 2010105728 A2 | 9/2010 |
| WO | 2022125116 A1 | 6/2022 |
| WO | 2024160342 A1 | 8/2024 |

OTHER PUBLICATIONS

Lee, et al., "Bioinspired artificial eyes: optic components, digital cameras, and visual prostheses", Advanced Functional Materials 28.24 (2018): 1705202.

Sahel, et al., "Partial recovery of visual function in a blind patient after optogenetic therapy", Nature Medicine, vol. 27, Jul. 2021, 1223-1229, www.nature.com/naturemedicine.

Thompson, et al., "Optical stimulation of neurons", Current Molecular Imaging, 2014, 3, 162-177.

Carroll, et al., "System and Method for Optical Stimulation", U.S. Appl. No. 19/044,388, filed Feb. 3, 2025.

\* cited by examiner

SYSTEM FOR PROJECTING A PATTERN OF INTEREST ONTO A RETINAL AREA OF A HUMAN EYE

CROSS-REFERENCE TO RELATED APPLICATIONS

The present application is a 371 US National Stage Entry of PCT International Application No. PCT/EP2020/058873, filed Mar. 27, 2020, which claims priority to PCT International Application No. PCT/EP2019/057965, filed Mar. 28, 2019, the entire contents of which are incorporated by reference herein.

TECHNICAL FIELD

The invention relates to a system for projecting a pattern of interest onto a retina of a human eye, in particular for projecting a pattern of interest onto an area of a retina of a human eye.

Technological Background Retinal malfunction, particular caused by degenerative retinal diseases, is a leading reason for visual impairment or even blindness.

For at least partially restoring a patient's visual function, it is known to modify a retinal area by making use of a retinal implant or in other words retinal prosthesis. In this regard, several different types of retinal implants are known, which are based on different working principles.

Retinal implants have in common that they are usually placed suprachoroidally, epiretinally or subretinally in the eye of the patient, such that they can replace i.e effect the damaged photoreceptors. In this regard, information about a visual scene is captured with a camera and then transmitted to an electrode array implanted in the retina.

Among common retinal implants, implants are known which comprise skin-penetrating wires. These wires introduce risks of infection and scarring. Thus, more modern implants use different wireless techniques, for instance by delivering power and visual information through inductive coils. Furthermore, it is known to deliver power inductively and visual information optically through the pupil of the eye, or to deliver both visual information and power optically.

A particularly beneficial type of wireless information transfer retinal implants is based on projecting stimulation patterns of infrared light into the eye. When the gaze direction is such that some part of the implants is illuminated by part of the pattern, the implant converts that part of the signal to electrical current that stimulates the retina accordingly.

The retinal implant is an array composed of stimulation electrodes or pixels. Each pixel has one or several photodiodes that capture the light delivered from a visual processor and converts it into electrical current for stimulation.

Several implant arrays can be placed in the subretinal space, typically in or close to the foveal area.

For projecting light or a light beam, respectively, into a human eye, it is known to use a projector device, such as augmented reality goggles. A projector of the projector device projects the light beam onto the human eye, wherein the light beam is far broader than the pupil of the human eye. That is, only a part of the light beam and hence of the picture irradiance to be transmitted is led into the eye through its eye pupil and towards the retina.

Retinal implants based on projection of infrared light, in fact, require a specific irradiance for correct operation. Thus, ordinary augmented reality goggles are unsuitable in combination with such designed retinal implants.

Alternatively, an approach, known as optogenetics, has been proposed to treat the residual retinal cells to restore their photosensitive behavior by gene therapy. Optogenetics refers to the combination of genetics and optics to control well-defined events within specific cells of living tissue. Optogenetics consists in (i) genetically modifying target cells in order to render them sensitive to light by the expression of exogenous photoreactive proteins in cellular membrane and (ii) providing illuminating device able to provide light to said photoreactive proteins.

In the following paragraphs of this patent, such a retinal area of the human eye that has been modified to restore photosensitive behavior through implantation of a retinal prosthesis or modification by optogenetics will also be referred to as "modified retinal area".

SUMMARY OF THE INVENTION

It is an object of the present invention to provide an improved system for projecting a pattern of interest onto a retinal areal of a human eye.

The above object is solved by means of a system for projecting a pattern of interest onto a retina of a human eye comprising the features of claim 1. Further preferred embodiments are presented in the dependent claims, the description and the figures.

Accordingly, a system for projecting a pattern of interest onto a retinal area of a human eye is suggested, containing a carrying frame for being worn by a patient, a camera for capturing an image, a projector device for projecting a pulsed light beam reflecting a pattern of interest into a human eye, and a processor device being in communication with the camera and the projector device, wherein the processor device is adapted for converting the image captured by the camera into the optical pattern of interest being basis for the pulsed light beam, wherein the projector device and the camera are attached to the carrying frame.

According to preferred embodiment, the invention relates to such a system wherein said retinal area of a human eye is modified retinal area (also referred herein as first area of the retina of a human eye).

Thereby, it is possible to capture information about a visual scene, hence an image, by the camera, utilize at least one camera image to generate an optical pattern, wherein preferably, the at least one captured image is converted into an optical pattern, and then transmit the optical pattern to a first area of the retina of a human eye under the form of pulsed output light beam emitted by the projector device. Said "optical pattern" is further referred to "first light signal" in the followings.

According to one specific embodiment, "modified retinal area" or "first area of the retina" refers to photosensitive electrode array of a photosensitive retinal implant implanted in the retina of a human eye.

Thereby, it is possible to capture information about a visual scene, hence an image, by the camera, utilize at least one camera image to generate an optical pattern, wherein preferably, the at least one captured image is converted into an optical pattern, and then transmit the optical pattern to a photosensitive electrode array of a photosensitive retinal implant implanted in the retina. The retinal implant, thus, can convert the optical pattern of interest into electrical current for stimulation of corresponding first retinal area. That is, there is no need for a power supply for the retinal implant as power is provided by conversion of light into current by the photosensitive pixels of the retinal implant. A patient having a retinal implant merely has to be supplied with such a system and carry the carrying frame. Thereby, is may be achieved that the retinal implant may be continuously and/or within predetermined intervals irradiated with the optical pattern of interest based on the conversion of presently captured images.

Alternatively, one optical pattern may be based on several captured images, for example by subtraction of several images.

According to another preferred embodiment, the carrying frame is provided in form of glasses, wherein lenses of the glasses are transparent or semi-transparent. This allows that not only light emitted by the projector device may reach the retina, but a person carrying the glasses may also be able to perceive optical input by means of ordinary vision, i.e. optical input from environment further called environment light signal. Accordingly, the scene perceived by the person may be a composition of ordinary vision and the optical pattern.

According to said preferred embodiment, the invention relates to a system as described above wherein it is possible to:
 capture information about a visual scene, hence an image, by the camera, utilize at least one camera image to generate a first light signal (i.e. an optical pattern), and then transmit the first light signal to a first area of the retina of a human eye, and
 wherein said system is further adapted to allow a second light signal of the environment (i.e. ordinary vision) to be transmitted to a second area of the retina of a human eye.

According to preferred embodiment, said second area of the retina is not modified retina area.

According to preferred embodiment, said first and second light signals are arranged so that the intersection between the first area and the second area is void.

According to another embodiment, said first and second light signals are arranged so that the second area surrounds the first area.

According to the invention said system is adapted to allow a second light signal of the environment (i.e. ordinary vision) to be transmitted to a second area of the retina of a human eye. More particularly the second light signal is as broad as possible compared to first light signal. Accordingly the projector device and the camera are attached to the carrying frame, more particularly to glasses, even more particularly to lenses of the glasses in such a way as to allow a second light signal of the environment (i.e. ordinary vision) as broad as possible to be transmitted to a second area of the retina of a human eye. This goal can be reached by selecting specific width and height of the projector device and/or of the camera attached to the carrying frame. By convention, widths are measured in the transversal direction, and heights are measured in the third (vertical) direction. According to preferred embodiment, the width of the projector device and/or of the camera attached to the carrying frame is less than about 70 millimeters, preferably less than about 50 millimeters, and even more preferably less than about 30 millimeters. According to preferred embodiment, the height of the projector device and/or of the camera attached to the carrying frame is less than about 20 millimeters, preferably less than about 15 millimeters, even more preferably less than about 10 millimeters, and most preferably less than about 5 millimeters. The term "about" as used herein means within 20%, preferably within 10%, and more preferably within 5%. In specific case, "about X", means "X".

According to special preferred embodiment, the projector device and/or of the camera attached to the carrying frame are made at least partially with a material that is transparent or translucent, more particularly transparent or translucent to visible light.

According to preferred embodiment, the camera and optics of the projector device are arranged in line on the carrying frame. According to another preferred embodiment, the carrying frame is provided in form of glasses and the camera and optics of the projector device are arranged in line put beam on both sides of one of the said glasses. Camera defines one main axis $Z_1$, and optics of the projector device defines main axis $Z_2$, according to preferred embodiment, main axis $Z_1$ and $Z_2$ are aligned lengthwise, in other words this means that main axis $Z_1$ of the camera is aligned with the center of the output light beam emerging from the optics of the projector device. According to the invention, the term "optics of the projector device" designates the optic elements of the projector that are projecting the output light beam, preferably pulsed light beam, corresponding to the optical pattern (i.e. the first light signal) onto the modified retinal area of the human eye.

According to a further preferred embodiment, the processor device is provided separate to the carrying frame, wherein a connection cable is provided for communication of the processor device with the camera and the projector device. Thereby, a total weight of the carrying frame comprising the projector device and the camera can be relatively low, as the processor device may be attached to the patient remote from the carrying frame, e.g. by means of a clip or shoulder strap. Preferably, the processor device is provided in the form of a pocket processor. Hence, a wearing comfort for a person carrying the carrying frame can be improved. Moreover, in that the processor device is provided separate to the carrying frame, the size and the weight of the processor device is not limited to requirements of e.g. wearing comfort for the carrying frame.

Alternatively, the processor device is arranged at the carrying frame, wherein preferably the processor device is integrated in the projector device. A such designed system may comprise a relatively compact design.

The system preferably further comprises a light source being adapted for providing an input light beam, preferably a pulsed input light beam, based on which the optical pattern of interest is formed.

According to a preferred embodiment, the light source is arranged in the projector device. A such designed system may be relatively compact, as connection cables for connecting the projector device and the light source may merely have to be provided within the projector device and/or can substantially be void.

Alternatively, the light source can be arranged in the processor device. Thereby, the total weight of the carrying frame can further be reduced compared to a system in which the light source is arranged at the carrying frame.

It has been proven beneficial when the light source contains a laser, a laser diode, and/or an LED, preferably an LED-Matrix, wherein preferably the light source is adapted to emit light having a wavelength in the infrared field, and/or coherent light or incoherent light.

Preferably, the system comprises a battery for providing power to the light source, the processor device and/or the projector device, wherein preferably the battery is preferably provided separate to the carrying frame, preferably located in the processor device. Thus, the battery does not add weight to the frame. Moreover, as the battery may be carried separate to the frame, a volume and/or a weight of the battery and, thus, a capacity of the battery may be bigger than a battery arranged at the carrying frame.

According to a further preferred embodiment, the processor device comprises a processor unit being adapted to provide controlling of a pulse duration and/or being adapted to provide controlling of a frequency and/or being adapted to provide controlling of a light intensity of the light beam (corresponding to the first light signal). Thereby, the light beam can be adjusted and/or modulated to match the requirements for reliable and safe operation of the system. In particular, the light beam may be adjusted for reliable operation of the respective retinal implant implanted in the patient's eye. Moreover, overstimulating of the remaining healthy photoreceptors of the retina can be avoided by controlling the light beam, in particular the total irradiance and/or irradiating time of the light beam hitting at the retina, as well as overstimulating the modified retinal area.

According to yet another preferred embodiment, the processor unit is adapted to provide controlling of a pulse duration and/or is adapted to provide controlling of a frequency and/or is adapted to provide controlling of a light intensity of the light source. Thereby, also an input light beam might be controlled, adjusted and/or matched.

The system preferably comprises a modulation micromirror array, preferably a digital micromirror device, which is preferably adapted for modulating and dividing a pulsed input light beam emitted by the light source into a modulated light pattern of modulated pulsed sub-beams, wherein an orientation of each of the micromirrors of the micromirror array is individually controllable based on a pattern of interest provided by the processor device, such that the sub-beams form a pulsed output beam reflecting the pattern of interest. With other words, only those of the micromirrors which are in an active state contribute to forming the output light beam.

Preferably, the input light beam is directed towards the modulation micromirror array by an optical prism, preferably a total internal reflection (TIR) prism.

According to another preferred embodiment, the modulation micromirror array is arranged in the projector device. Thereby, a robust and reliable design for providing the reflected pattern can be provided.

According to a preferred alternative, the modulation micromirror array is arranged in the processor device. Thereby, the total weight of the projector device and hence the carrying frame comprising the projector device and the camera can be further reduced. The output beam generated by the micromirror array is preferably directed into an optical fiber or an optical cable, wherein the optical fiber or the optical cable guides the output light beam emitted by the modulation micromirror array into the projector device for projecting the optical pattern of interest towards the human eye.

The connection cable is preferably adapted to convey data between the processor device and the projector device, and/or preferably the connection cable is adapted for providing electric power from the processor device to the camera and/or the projector device, and/or preferably the connection cable is adapted to convey light from the processor device to the projector device, wherein preferably the connection cable comprises an electrical cable and/or an optical fiber or an optical cable. The connection cable may preferably be adapted to convey camera image data and/or patterning data and/or data related for controlling the micromirror array.

The modulation micromirror array preferably is arranged adjacent to a prism, preferably a total internal reflection (TIR) prism, wherein the input light beam is directed towards the modulation micromirror array by the prism and/or the output light beam is directed to an outlet of the projector device, preferably a lens unit of the projector device.

According to yet another preferred embodiment, the light source is arranged in the processor device, wherein the connection cable comprises the electrical cable and the optical fiber or optical cable, wherein the optical fiber or optical cable provides connection of the light source with the projector device. Hence, both the input light beam and the control commands for controlling the alignment device and/or the modulation micromirror array can be created in the processor unit and are guided to the projector device via the connection cable.

Preferably, the projector device comprises a battery or an accumulator for providing the electrical components of the system with electric power. Thereby, the system can be carried by a person without the need of an additional connection to a stationary power supply.

When the connection cable and/or the projector device comprise an optional light safety interlock loop, preferably a laser safety interlock loop, safety of the system can further be increased, as via the light safety interlock loop, personnel may be prevented from accidental exposure to hazardous lasers. Preferably, the light safety interlock loop comprises or is connected to a switch which is adapted to disable light emission by the light source, light conduction through the connection cable, and/or light projection by the projector device, if the loop is open, e.g. due to a corrupted or defect light conducting element, for example an optical fiber or optical cable conducting the light emitted by the light source.

For maximum safety and efficiency, the light safety interlock loop may preferably be configured to provide automatic shut-off of the light beam in case a failure is detected.

The projector device may further comprise optional optic elements for projecting the light beam corresponding to the optical pattern (i.e. first light signal) from the exterior of a human eye at a pupil of the eye, wherein preferably these optic elements are configured such that an exit pupil diameter of the light beam is set smaller than an eye pupil diameter of the eye, wherein the latter is preferably achieved by setting the exit pupil diameter equal to or smaller than 3 mm, preferably equal to or smaller than 2 mm, more preferably equal to or smaller than 1 mm, particularly preferably equal to or smaller than 0.5 mm, and particularly preferably the exit pupil diameter is set to 1 mm, 0.75 mm, 0.5 mm, or 0.25 mm, and/or in that the optics comprise an optional adjustment unit for adjusting the exit pupil diameter based on a monitored value of the eye pupil diameter and/or of the ambient light intensity detected via an optional sensor unit.

According to another preferred embodiment, the system comprises an alignment device for adjusting a position and/or orientation of the projector device with respect to the carrying frame, wherein preferably the alignment device is formed such that the projector device can be moved relative to the carrying frame in a plurality of movement directions, particularly preferably in five movement directions.

According to a further preferred embodiment, the system comprises an eye tracking mechanism that monitors the eye position and/or angle, and the alignment device is configured for automatically aligning the projector device (i.e. main axis $Z_2$) with the eye axis, wherein preferably, the alignment device is motorized and/or the alignment device comprises tilting mirrors and/or piezoelectric motors, and/or a coupling feedback mechanism that automatically aligns the projector device with the eye axis.

According to special embodiment, the camera is integrated into the projector device, wherein preferably, the camera and the output beam of the projector device are aligned to each other.

It has been proven beneficial when the carrying frame contains a spectacles frame, and/or wherein the frame contains a headband, and/or wherein the frame contains a headring and/or a flexible band.

According to yet another preferred embodiment, the processor device may comprise one or several electronic boards, a port for detachable connection to the connection cable, preferably a plug or a socket, and/or a user interface, preferably comprising buttons allowing the patient to tune the perception versus the constraints of the environment, for instance an ON/OFF button, and/or a button for changing an image processing mode, changing the brightness, a zoom, and/or an audio volume level, and/or LEDs.

Furthermore, the processor device may comprise an optional port, for instance a USB port, for enabling connection to an external device, for instance a PC, an/or the processor device comprises a wireless communication unit, preferably configured for communication via WiFi, WLAN, Bluetooth or ZigBee, wherein preferably, the wireless communication unit is configured for secured communication, preferably containing encryption and/or security protocols.

Moreover, the processor device may preferably comprise housing for housing at least parts of the other components of the processor device. Preferably, the housing at least provides dust and water protection, preferably at least according to IP 22.

Alternatively or in addition, the projector device may preferably comprise housing for housing at least parts of the other components of the projector device. Preferably, the housing at least provides dust and water protection, preferably at least according to IP 22.

According to yet another preferred embodiment, the projector device comprises a port for detachable connection to the connection cable.

According to another embodiment, the carrying frame comprises a lens, wherein preferably, the lens is arranged at the frame to cover the eye when the frame is worn by a person. The lens preferably is shaded, preferably tinted. By providing the shaded lens, the eye pupil diameter may naturally be enlarged as less ambient light falls into the eye pupil. Hence, alignment by the alignment device may be facilitated.

BRIEF DESCRIPTION OF THE DRAWINGS

The present disclosure will be more readily appreciated by reference to the following detailed description when being considered in connection with the accompanying drawings in which.

DETAILED DESCRIPTION OF PREFERRED EMBODIMENTS

In the following, the invention will be explained in more detail with reference to the accompanying figures. In the figures, like elements are denoted by identical reference numerals and repeated description thereof may be omitted in order to avoid redundancies.

Figure 1:
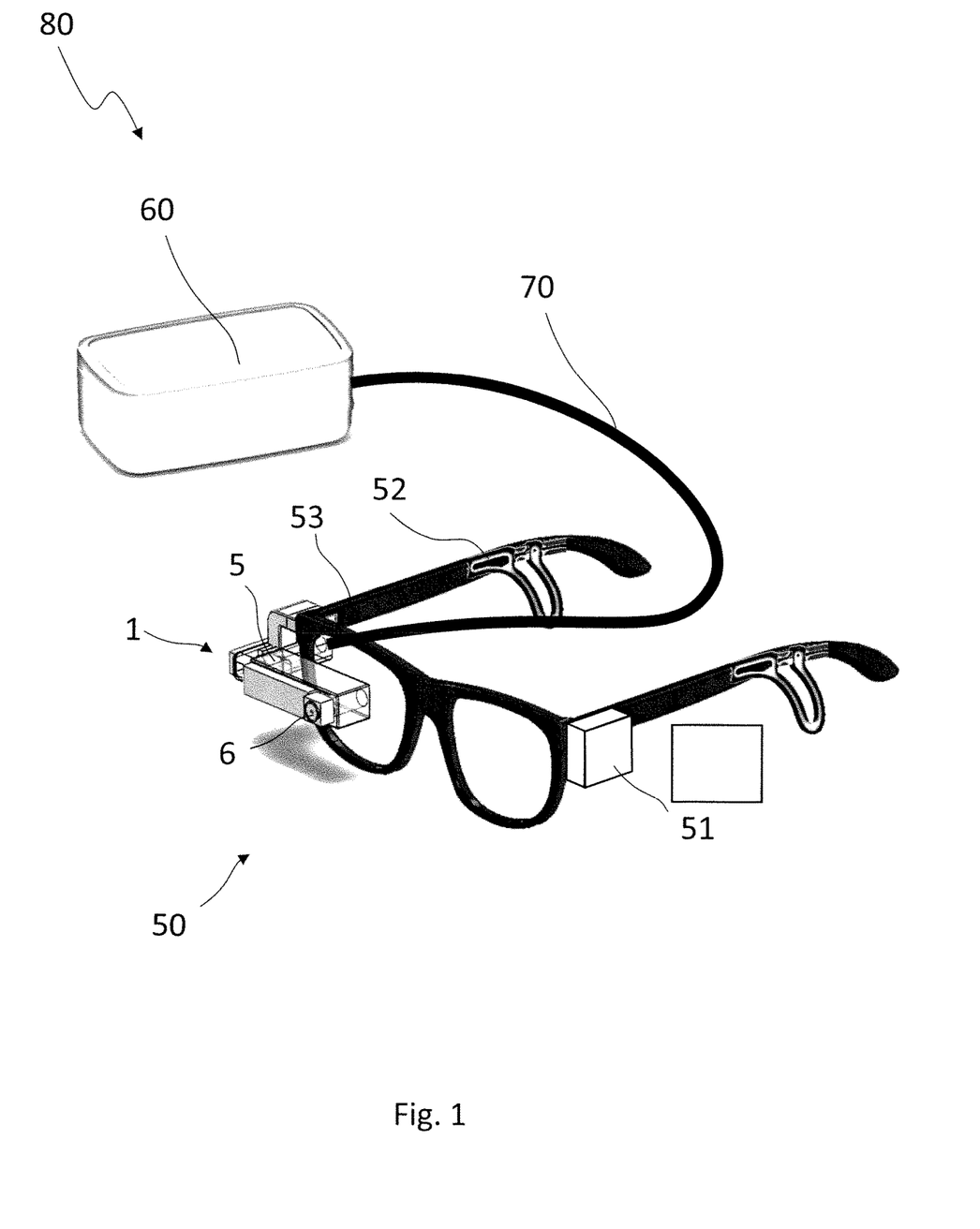
FIG. 1 is a schematic perspective side view of a system for projecting an optical pattern of interest onto a human eye according to a first embodiment.

FIG. 1 is a schematic perspective side view of a system 80 for projecting an optical pattern of interest onto a retina of a human eye according to a preferred embodiment. The system 80 comprises a carrying frame 50 which substantially comprises the form of a spectacles frame and which can be worn by a patient having a photosensitive retinal implant implanted into his eye or having a genetically modified retinal area. The system 80 further contains a projector device 1 which is adapted for projecting a pulsed output light beam which reflects the optical pattern of interest into the human eye, and a camera 6 for capturing an image. According to this preferred embodiment, the camera 6 is integrated and/or is aligned with the projector device 1. It must be noticed that in the followings the term "projector device" can designate the combination of the projector device with the camera present in the system. The projector device 1 is attached to the carrying frame 50 via a fastening section 5.

The projector device 1 is in communication with a processor device 60 by means of a connection cable 70. The processor device 60 is arranged separate to the carrying frame 50 and the projector device 1.

According to this embodiment, the projector device 1 comprises an integrated light source (not shown in this figure) which emits coherent laser light in the near infrared field, in this exemplary embodiment in a wavelength of 880 nm. Alternatively, the light may comprise any other wavelength suitable for interaction with a respective photosensitive retinal implant or genetically modified retinal cells.

According to another preferred embodiment, the light source is provided in form of an LED emitting incoherent light, preferably in the near infrared field.

The projector device 1 furthermore comprises a modulation micromirror array 3 (see FIG. 2), according to this preferred embodiment provided in form of a digital micromirror device. The modulation micromirror array 3 is adapted for modulating and dividing a pulsed input light beam emitted by the light source into a modulated light pattern consisting of modulated pulsed sub-beams, as will be explained in more detail with respect to FIG. 2.

The processor device 60 is in communication with the camera 6 and the projector device 1 via a cable 70. The processor device 60 furthermore is adapted for converting an image captured by the camera 6 into the pattern of interest which serves as the basis for the pulsed output light beam emitted by the projector device 1 (also named optical pattern in the specification).

Figure 2:
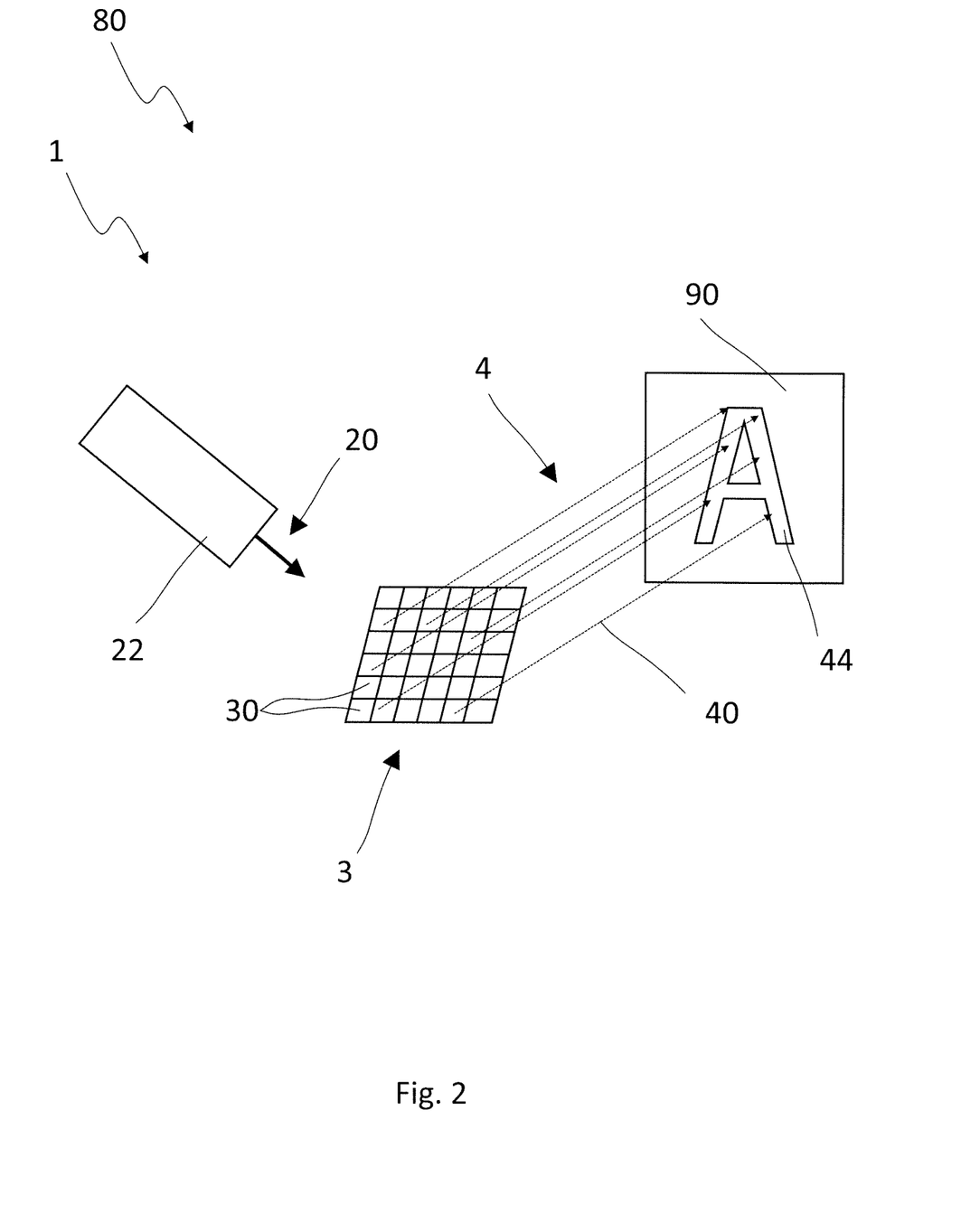
FIG. 2 shows a schematic operation principle for projecting an optical pattern of interest on a photosensitive retinal implant of a human eye.

Hence, via the light source, the collimated high-power input light beam is generated, directed through a TIR prism, such that it hits the active area of the modulation micromirror array 3 (FIG. 2). The active area here is constituted by those of the micromirrors of the micromirror array 3 which are oriented such that the modulated sub-beams forming the pattern are redirected through the TIR prism again and through a final lens, such that they leave the projector device 1 in form of the output beam towards and into the eye.

With other words, the processor device 60 uses the image taken by the camera 6 to form an optical pattern of interest. The processor device 60 allocates the micromirrors of the micromirror array 3 to one or more pixels of the pattern of interest and controls the orientation of each micromirror, such that the reflected sub-beams constituting the output beam reflect the optical pattern of interest.

FIG. 2 shows a schematic operation principle for projecting the optical pattern of interest 44 on the photosensitive retinal implant 90 of a human eye as described above. The light source 22 provides the pulsed input light beam 20 which is directed onto the modulation micromirror array 3 comprising the plurality of micromirrors 30 which can individually be controlled by the processor device 60 such that an orientation of each of the micromirrors 30 can individually be adjusted. Alternatively, the micromirrors 30 may be controlled and/or adjusted in sub-groups.

As described above, by means of the micromirror array 3, the input light beam 20 is modulated, thereby forming a first light signal or output beam 4 corresponding to the optical pattern. The orientation of the micromirrors 30 is individually adjusted by means of control commands from the processor device 60, such that the optical pattern of interest 44 which is to be projected onto the retinal implant 90 can be reflected by the plurality of sub-beams 40.

In this regard, the optical pattern of interest 44 is based on the content or image captured by the camera 6 which has been processed into a digital pattern of pixels by the processor device 60.

Hence, the first light signal or output beam 4 substantially reflects the optical pattern of interest 44. When the output beam 4 hits the retinal implant 90, only those parts of the retinal implant 90 are illuminated by means of the output beam 4 or in particular the sub-beams 40, which reflect the optical pattern of interest 44 at the retinal implant 90. Consequently, only those photosensitive diodes of the retinal implant 90 convert light into electric current, which are arranged in the projected optical pattern of interest 44. A person comprising the retinal implant 90, thus, can perceive the optical pattern of interest 44.

The carrying frame 50 comprises optional ear pads 52 which are displaceable along the temples 53 of the frame 50 such that the carrying frame 50 can be adjusted to a person's head size and/or other morphology characteristics, such as ear position and shape. The optional ear pads 52 can be configured to prevent the frame 50 to move with respect to the ear of a person wearing the frame 50. Hence, the earpads 52 may function as earstops.

The projector device 1 is arranged at the left side of the carrying frame 50, such that light is projected into the left eye of the patient wearing the carrying frame 50. A counterweight 51 is arranged on the side of the frame 50 opposite to the side at which the projector device 1 is arranged such that the lateral weight distribution of the carrying frame 50 is balanced.

Alternatively or in addition, a projector device 1 may be arranged at the right side of the carrying frame 50, such that light is projected into the right eye of the patient wearing the carrying frame 50. Preferably, the projector devices 1 are the same for both left and right configurations, wherein preferably, a first projector device 1 is mounted with 180° rotation difference with regard to a second projector device 1.

Figure 3:
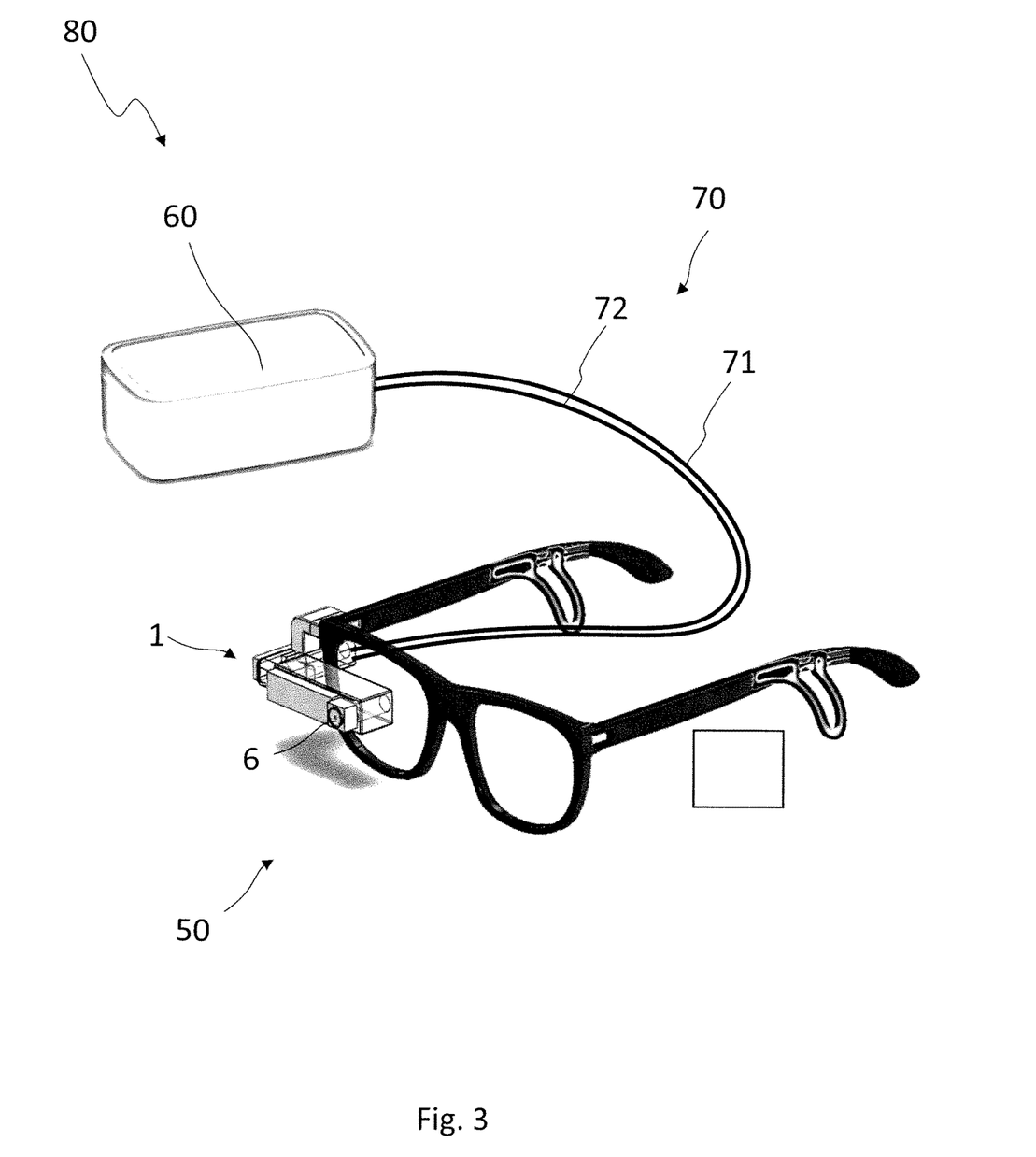
FIG. 3 schematically shows a system for projecting an optical pattern of interest onto a retina of a human eye according to another preferred embodiment.

FIG. 3 shows a system 80 for projecting an optical pattern of interest onto a retina of a human eye according to another preferred embodiment. The system 80 substantially corresponds to the system shown in FIG. 1, wherein in this embodiment, the light source is arranged in the processor device 60. The connection cable 70, thus, comprises an electrical cable 71 for providing electric power and control commands to the projector device 1 and to the camera 6 and also a camera stream from the camera 6 to the processor device 60, and an optical fiber 72 to convey light emitted by the light source from the processor device 60 to the projector device 1. With other words, the connection cable 70 is a hybrid cable providing both electrical and optical conduction. With other words, both electrical and optical information is conducted via connection cable 70.

Furthermore, the connection cable 70 comprises a laser safety interlock loop (not shown). By means of the laser safety interlock loop, a damage to the connection cable 70 can be detected. In case the laser safety interlock loop is open due to a damage, for instance, of the optical fiber 72, a switch (not shown) arranged in the processor device 60 interrupts connection between the light source arranged in the processor device 60 and the connection cable 70.

Figure 4:
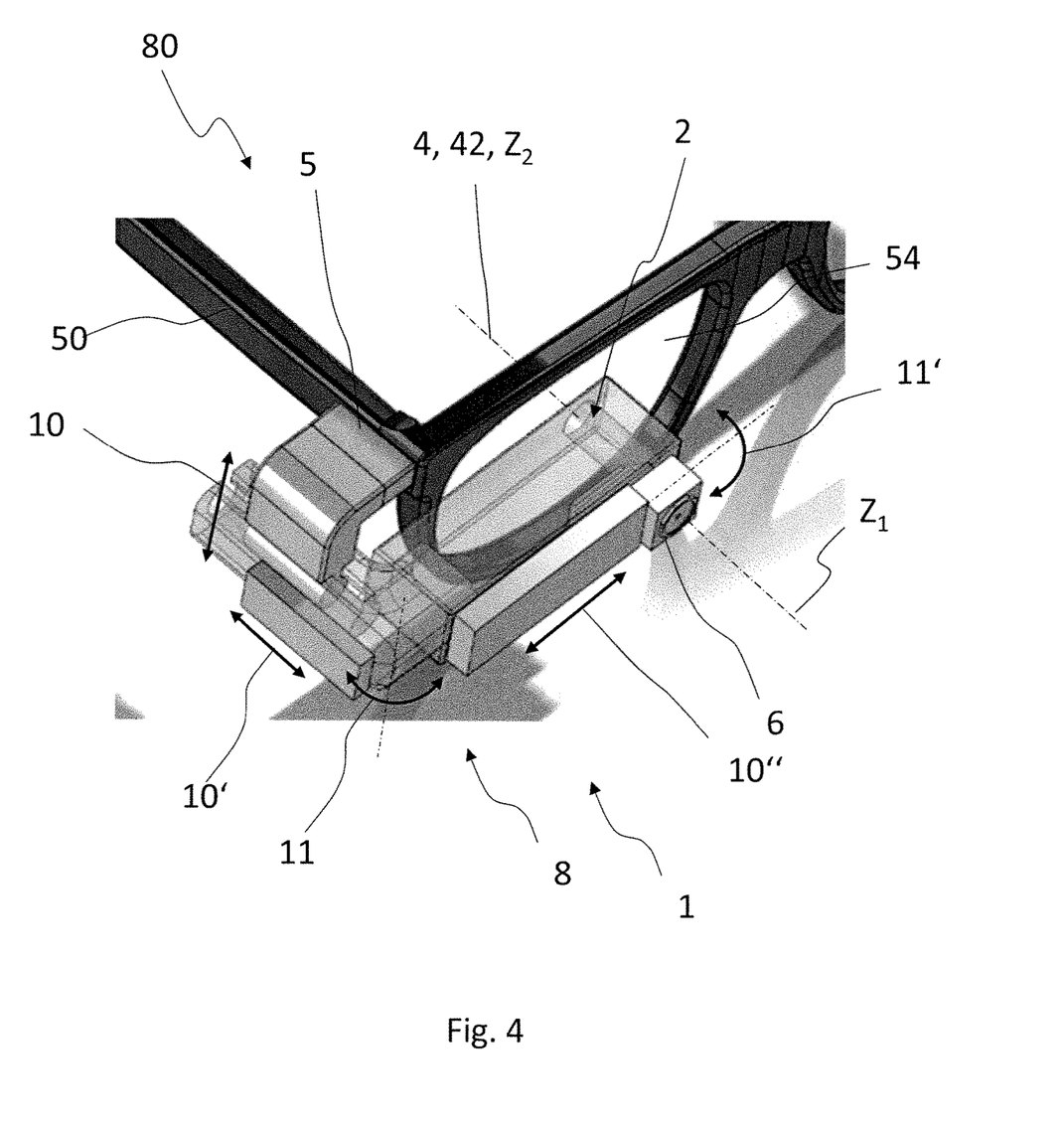
FIG. 4 schematically shows a perspective side view of a detail of a carrying frame according to another preferred embodiment.

FIG. 4 schematically shows a perspective side view of a detail of a carrying frame 50 according to another preferred embodiment. The projector device 1 comprises an alignment device 8 by means of which the position and the orientation of output light beam 4 can be adjusted with respect to the carrying frame 50, thus with respect to the human eye of the patient wearing the carrying frame 50.

The alignment device 8 is formed such that optics 2 through which the light beam 4 exits the projector device 1 can be moved relative to the fastening section 5 in five movement directions 10, 11.

Three movement directions are longitudinal directions 10, 10', 10", wherein optionally each longitudinal direction is oriented substantially orthogonal to the other longitudinal directions. In this exemplary embodiment, a first longitudinal movement direction 10 corresponds to a longitudinal axis of a human head, a second longitudinal movement direction 10" corresponds to a transversal axis of a human head, and a third movement longitudinal direction 10' corresponds to a sagittal axis of a human head. The two remaining movement directions are directions of rotation 11, 11'. In this exemplary embodiment, a first direction of rotation 11' is oriented such that a pantoscopic angle of the optics 2 with respect to the eye can be adjusted, and a second direction of rotation 11 is oriented such that a wrap angle of the optics 2 with respect to the eye can be adjusted.

For providing the movement directions 10, 10', 10", 11, and 11', the alignment device 8 comprises a plurality of kinematic pairs which are shown in generic form, as kinematic pairs are per se known. The longitudinal movement directions 10, 10', 10" are provided by means of prismatic joints. In detail, one of the prismatic joints is arranged in proximity to the fastening section 5. This prismatic joint provides linear movement in the longitudinal movement direction 10. A second prismatic joint is arranged adjacent to the first prismatic joint and provides movement along the longitudinal movement direction 10'. Adjacent thereto, a first rotating joint is arranged, which provides rotation in the direction of rotation 11. Moreover, a further prismatic joint is provided for enabling movement in longitudinal movement direction 10". In addition, a further rotational joint is provided for providing rotation in direction of rotation 11'.

Furthermore, alignment device 8 comprises a plurality of locking units, wherein each of the locking units (not shown) is allocated to a respective kinematic pair for locking or releasing movement in the respective movement direction. Locking units are per se known, and for instance may be implemented in the form of a locking screw or a surface comprising a high coefficient of friction.

Preferably, the carrying frame comprises a rigid design to ensure robust positioning. Alternatively, the carrying frame comprises at least a robust part to ensure robust and repeatable placement in front of the eye, while some other part of the frames, e.g. the temples, may be provided be more flexible to accommodate different patient's head sizes or other morphology adjustments while keeping a robust positioning.

As can be seen in FIG. 4, the main axis $Z_1$ of the camera 6 is aligned with a main axis $Z_2$ of the optics 2 and hence with the center 42 of the output light beam 4. According to this exemplary embodiment, the main axis $Z_2$ and the main axis $Z_1$ are concentrically aligned. With other words, the camera 6 and the optics 2 are arranged in line facing opposite sides of the projector device 1.

The frame 50 furthermore comprises optional lenses 54 which according to this embodiment are shaded, here tinted. By providing the tinted lens 54, the eye pupil diameter is naturally enlarged as less ambient light falls into the eye pupil such that alignment by the alignment device is facilitated.

LIST OF REFERENCE NUMERALS 1 projector device
2 optics
$Z_2$ main axis of the optics
5 fastening section
6 camera
$Z_1$ main axis of camera
8 alignment device
10 longitudinal movement direction
11 direction of rotation
20 input light beam
22 light source
3 micromirror array
30 micromirror
4 output beam
40 sub-beam
42 center of the light beam
44 pattern of interest
50 frame
51 counter weight
52 earpad
53 temple
54 lens
60 processor device
70 connection cable
71 electric cable
72 optical fiber
80 system
90 retinal implant

The invention claimed is:

1. A system for projecting an optical pattern of interest onto a modified retinal area of a human eye, the system comprising:
a carrying frame for being worn by a patient;
a camera for capturing an image;
a projector device for projecting a pulsed light beam reflecting a pattern of interest onto the modified retinal area of the human eye, the pulsed light beam derived from the image captured by the camera, the projector device comprising a light source;
a modulation micromirror array for modulating and dividing a pulsed input light beam emitted by the light source into a modulated light pattern of modulated pulsed sub-beams, wherein an orientation of each micromirror of the modulation micromirror array is individually controllable or controlled by sub-groups based on the pattern of interest, such that the modulated pulsed sub-beams form a pulsed output beam reflecting the pattern of interest, wherein the pulsed input light beam is directed towards the modulation micromirror array by an optical prism;
an alignment device for adjusting a position and an orientation of the projector device with respect to the carrying frame and with respect to an axis of the human eye; and
a processor device being in communication with the camera and the projector device, wherein the processor device is adapted for converting images captured by the camera into patterns of interest used as a basis for the pulsed light beam;
wherein the projector device and the camera are attached to the carrying frame,
wherein the camera and optics of the projector device are arranged facing opposite sides of the projector device such that the optics face toward the human eye and the camera faces away from the human eye and the camera and optics being arranged such that an axis of the camera and an axis of the optics are aligned lengthwise and concentric, and
wherein the system is configured to operate such that the pulsed light beam is projected onto the modified retinal area of the human eye while keeping the axis of the camera and the axis of the optics aligned.

2. The system according to claim 1, characterized in that the processor device is provided separate to the carrying frame, wherein a connection cable is provided for communication of the processor device with the camera and the projector device.

3. The system according to claim 2, wherein the connection cable is adapted to convey data between the processor device and the projector device and/or to convey camera data, and/or the connection cable is adapted for providing electric power from the processor device to the camera and/or the projector device, and/or the connection cable is adapted to convey light from the processor device to the projector device, wherein the connection cable comprises an electrical cable, an optical fiber, and/or an optical cable.

4. The system according to claim 3, wherein the connection cable comprises the electrical cable and the optical fiber and/or optical cable.

5. The system according to claim 2, characterized in that the connection cable and/or the projector device comprise a light safety interlock loop.

6. The system according to claim 2, characterized in that the connection cable and/or the projector device comprise a laser safety interlock loop.

7. The system according to claim 1, wherein the light source contains a laser, a laser diode, an LED, and/or an LED-Matrix, wherein the light source is adapted to emit light having a wavelength in the infrared field, and/or coherent light or incoherent light.

8. The system according to claim 1, characterized in that the processor device comprises a processor unit being adapted to provide controlling of a pulse duration and/or a frequency and/or light intensity of the pulsed light beam and/or of the light source.

9. The system according to claim 1, wherein the modulation micromirror array is arranged in the projector device, or wherein the modulation micromirror array is arranged in the processor device.

10. The system according to claim 1, wherein the alignment device is formed such that the projector device can be moved relative to the carrying frame in a plurality of movement directions, including five movement directions.

11. The system according to claim 1, wherein the carrying frame contains a spectacles frame, and/or wherein the carrying frame contains a headband, and/or wherein the carrying frame contains a headring and/or a flexible band.

12. The system according to claim 1, wherein the carrying frame comprises a lens, wherein the lens is shaded or tinted.

13. The system according to claim 1, wherein the optical prism comprises a total internal reflection prism.

14. A system for projecting an optical pattern of interest onto a modified retinal area of a human eye, the system comprising:
- a carrying frame for being worn by a patient;
- a camera for capturing an image;
- a projector device for projecting a pulsed light beam reflecting a pattern of interest onto the modified retinal area of the human eye, the pulsed light beam derived from the image captured by the camera;
- an alignment device for adjusting a position and an orientation of the projector device with respect to the carrying frame and with respect to an axis of the human eye; and
- a processor device being in communication with the camera and the projector device, wherein the processor device is adapted for converting images captured by the camera into patterns of interest used as a basis for the pulsed light beam;

wherein the projector device and the camera are attached to the carrying frame, wherein the camera and optics of the projector device are arranged facing opposite sides of the projector device such that the optics face toward the human eye and the camera faces away from the human eye and the camera and optics being arranged such that an axis of the camera and an axis of the optics are aligned lengthwise and concentric, wherein the system is configured to operate such that the pulsed light beam is projected onto the modified retinal area of the human eye while keeping the axis of the camera and the axis of the optics aligned;

wherein the optics are configured for projecting the light beam from the exterior of a human eye at a pupil of the eye, and wherein the optics are configured such that an exit pupil diameter of the light beam is set smaller than an eye pupil diameter of the eye.

15. A system for projecting an optical pattern of interest onto a modified retinal area of a human eye, the system comprising:
- a carrying frame for being worn by a patient;
- a camera for capturing an image;
- a projector device for projecting a pulsed light beam reflecting a pattern of interest onto the modified retinal area of the human eye, the pulsed light beam derived from the image captured by the camera;
- an eye tracking mechanism that monitors the eye a position and/or angle of the human eye;
- an alignment device for adjusting a position and an orientation of the projector device with respect to the carrying frame and with respect to an axis of the human eye, wherein the alignment device is configured for automatically aligning the projector device with a central eye axis, wherein the alignment device is motorized and/or the alignment device comprises tilting mirrors and/or piezoelectric motors, and/or a coupling feedback mechanism that automatically aligns the projector device with the central eye axis; and
- a processor device being in communication with the camera and the projector device, wherein the processor device is adapted for converting images captured by the camera into patterns of interest used as a basis for the pulsed light beam;

wherein the projector device and the camera are attached to the carrying frame, wherein the camera and optics of the projector device are arranged facing opposite sides of the projector device such that the optics face toward the human eye and the camera faces away from the human eye and the camera and optics being arranged such that an axis of the camera and an axis of the optics are aligned lengthwise and concentric, wherein the system is configured to operate such that the pulsed light beam is projected onto the modified retinal area of the human eye while keeping the axis of the camera and the axis of the optics aligned.

* * * * *

UNITED STATES PATENT AND TRADEMARK OFFICE
CERTIFICATE OF CORRECTION

| | | |
|---|---|---|
| PATENT NO. | : 12,403,040 B2 | Page 1 of 1 |
| APPLICATION NO. | : 17/593274 | |
| DATED | : September 2, 2025 | |
| INVENTOR(S) | : Guillaume Buc et al. | |

It is certified that error appears in the above-identified patent and that said Letters Patent is hereby corrected as shown below:

In the Claims

Column 14, Line 15, In Claim 15, after "monitors", delete "the eye"

Signed and Sealed this
Seventh Day of October, 2025

John A. Squires
*Director of the United States Patent and Trademark Office*